United States Patent [19]

Daniels et al.

[11] Patent Number: 4,933,281
[45] Date of Patent: Jun. 12, 1990

[54] METHOD FOR PRODUCING RHAMNOSE

[75] Inventors: Lacy Daniels, Coralville; Robert J. Linhardt, Iowa City; Barbara A. Bryan, Glenview, all of Iowa; Friedrich Mayerl, Thonex; Wilhelm Pickenhagen, Chavannes-des-Bois, both of Switzerland

[73] Assignee: The University of Iowa Research Foundation, Iowa City, Iowa

[21] Appl. No.: 26,857

[22] Filed: Mar. 17, 1987

[51] Int. Cl.$^5$ .............. C12P 19/04; C07G 17/00; C12R 1/01; C12R 1/38
[52] U.S. Cl. .................. 435/101; 435/875; 435/874; 435/822; 536/123
[58] Field of Search .............. 435/101, 134, 146, 148, 435/155, 875, 822, 874; 536/124, 123

[56] References Cited

U.S. PATENT DOCUMENTS 4,326,053 4/1982 Kang et al. .................. 536/123
4,628,030 12/1986 Kaeppeli et al. ............. 435/101

FOREIGN PATENT DOCUMENTS

A-0102535 3/1984 European Pat. Off. .
A-2110410 6/1972 France .
DD-A-234689 4/1986 German Democratic Rep. .

OTHER PUBLICATIONS

Syldatk et al., "Production of Four Interfacial Active Rhamnolipids from n-Alkanes or Glycerol by Resting Cells of *Pseudomonas species*, DSM 2874", *Z. Naturforsch.*, 40:61–67 (1985) [Syldatk et al., I].
Syldatk et al., "Chemical and Physical Characterization of Four Interfacial-Active Rhamnolipids from *Pseudomonas spec.*, DSM 2874, Grown on n-Alkanes", *Z. Naturforsch* 40:51–60 (1985) [Syldatk et al., II].
Bryan et al., "Variation in Composition and Yield of Exopolysaccharides Produced by *Klebsiella sp.*, Strain K32 and *Acinetobacter calcoaceticus*", *Appl. Environ. Micro.*, 51:1304–08 (1986).
Guerra-Santos et al., "*Pseudomonas aeruginosa* Biosurfactant Production in Continuous Culture with Glucose as Carbon Source", *Appl. Environ. Micro* 48:3301–05 (1984).
Taylor et al., "Pathways for Biosynthesis of a Bacterial Capsular Polysaccharide", 81:688–93 (1960).
Reiling et al., "Pilot Plant Production of Rhamnolipid Biosurfactant by *Pseudomonas aeruginosa*", *Appl. Environ. Micro.*, 51:985–89 (1986).
Hauser et al., "Studies on the Production of Glycolipid by *Pseudomonas aeruginosa*", 68:645–53 (1954).
Hisatsuka et al., "Formation of Rhamnolipid by *Pseudomonas aeruginosa* and Its Function in Hydrocarbon Fermentation, ", Agr. Biol. Chem., 35:686–92 (1971).
Jarvis et al., "A Glyco-Lipide Produced by *Pseudomonas Aeruginosa*," 71:4124–26 (1949).
Edwards et al., "Structure of a Rhamnolipid From *Pseudomonas aeruginosa*", *Arch. Biochem. Biophys.*, 111:415–21 (1965).
Guerra-Santos et al., "Dependence of *Pseudomonas aeruginosa* Continuous Culture Biosurfactant Production on Nutritional and Environmental Factors", *Appl. Microbiol. Biotechnol.*, 24:443–48 (1986), [Guerra-Santos et al., II].
Cooper et al., "Production of a Biosurfactant from *Torulopsis bombicola*", *Appl. Environ. Micro.*, pp. 173–176, 1984.
*Chem. Abst.*, Hokkaido, Aug. 17, 1987, p. 406, #55423(y).
*Chem. Abst.*, Kappeli et al., Jun. 10, 1985, p. 800, #202612(m).
*Chem. Abst.*, Hirayama, et al., Jun. 7, 1982, #196234(d).

Primary Examiner—Ronald W. Griffin
Assistant Examiner—Pamela S. Webber
Attorney, Agent, or Firm—Seed and Berry

[57] ABSTRACT

A method for large-scale production of rhamnose and 3-hydroxydecanoic acid is disclosed comprising the steps of growing microorganisms of *Pseudomonas sp.* capable of production of high levels of rhamnolipid in a defined culture medium containing vegetable oil. Additional steps include isolating the rhamnolipid from the culture medium, hydrolyzing the rhamnolipid to produce rhamnose and 3-hydroxydecanoic acid, and separating the rhamnose from the acid. Corn oil is the preferred vegetable oil and *Pseudomonas aeruginosa* is the preferred *Pseudomonas sp.* Non-limiting concentrations of nitrogen compounds and magnesium compounds and limiting concentrations of iron compounds are additionally preferably included in the culture medium.

33 Claims, 1 Drawing Sheet

COMPOUND:   SUBSTITUENT:

R1   $R^1$ = CH[(CH$_2$)$_6$CH$_3$]CH$_2$CO$_2$H   $R^2$ = H

R2   $R^1$ = H   $R^2$ = H

R3   $R^1$ = CH[(CH$_2$)$_6$CH$_3$]CH$_2$CO$_2$H   $R^2$ =

R4   $R^1$ = H   $R^2$ =

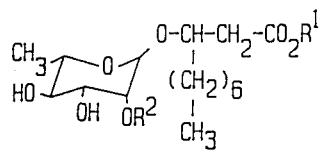
FIG.1
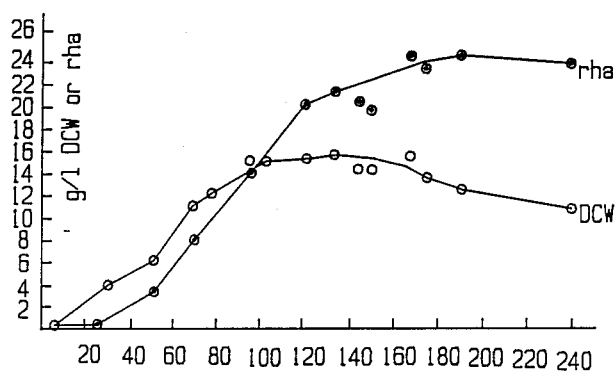
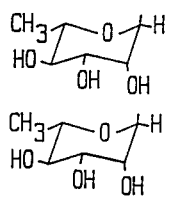
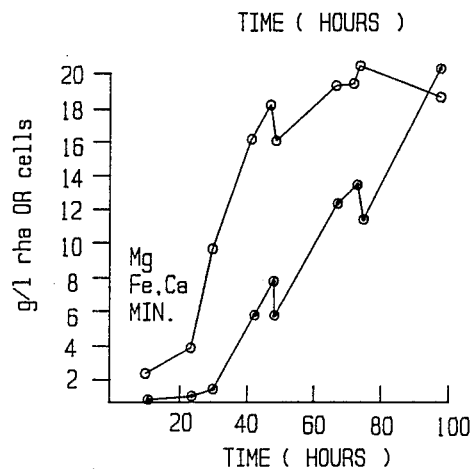
FIG.2
FIG.3

METHOD FOR PRODUCING RHAMNOSE

DESCRIPTION

1. Technical Field

The present invention relates generally to methods for production of rhamnose from rhamnolipid and specifically to large-scale production of rhamnose employing vegetable oil as a source of carbon and strains of Pseudomonas sp. as a microbial source.

2. Background Art

The sugar rhamnose is used as a fine chemical in scientific and industrial settings, as a component in chemical reactions, and as an intermediate in the synthesis of organic compounds. Present methods for the commercial preparation of rhamnose require extraction of quercetrin from oak bark, naringin from citrus peels, or rutin (quercetin-3-rutinoside) from oak bark or a variety of plants, such as buckwheat. Quercetrin, naringin, and rutin molecules possess a rhamnose portion and an aromatic portion, and rhamnose is generated by the hydrolysis of the rhamnose portion of the particular molecule. Several disadvantages accompany the labor-intensive processes for extraction of quercetrin, naringin, and rutin, including the production of large quantities of potentially toxic, aromatic waste products and the need for toxic or corrosive chemicals in the extraction process. Further, the bulky raw materials used for extraction must be harvested and then either transported at some expense to the extraction facility, or the processing plant must be located in proximity to the raw materials.

Another potential source of rhamnose is rhamnose-containing polysaccharides produced by plants or microorganisms. Certain polysaccharides (agar and gelrite) are characterized by gelling or thickening properties, while others may be used as emulsifiers. Further, some polysaccharides have been used as a source of useful monosaccharides.

The growth of certain bacteria results in the production of extracellular polysaccharides. B. A. Bryan et al, *Appl. Environ. Microbiol.* 51:1304-1308, 1986. This extracellular polysaccharide may be present as a capsule around the perimeter of the cell or may be released into the growth medium as slime, or may be present in both capsular and released form.

For instance, production of a *Pseudomonas elodea* polysaccharide containing 30% rhamnose was reported at yields of 1.5% "gel" from growth in 3% glucose. K. S. Kang and G. T. Veeder, U.S. Pat. No. 4,326,053. Fermentation of *Acinetobacter calcoaceticus* has been previously reported to yield polysaccharide containing 80% rhamnose at 0.5 g/1. W. H. Taylor and E. Juni, *J. Bacteriol.* 81:688-693, 1961. Higher yields of rhamnose have been reported from polysaccharides obtained from a specific strain of Acinetobacter and from Klebsiella sp. Bryan et al., supra.

One disadvantage to the production of rhamnose from polysaccharides is that isolated polysaccharides often contain other sugars in addition to rhamnose. Although hydrolysis of such polysaccharides yields rhamnose, the rhamnose product is often contaminated with the other sugars that were present in the polysaccharide.

A second disadvantage arises from an inherent property of polysaccharide itself. For instance, if microbial strains selected for elevated production of exopolysaccharide are employed as the source of rhamnose-containing polysaccharide, the release of polysaccharide into the growth medium results in a culture with high viscosity. This viscous suspension requires additional amounts of energy for the necessary agitation of the culture medium. In addition, the delivery of desired amounts of oxygen and other gases or of additional nutrients becomes more difficult in a viscous medium. In general, the high viscosity of the culture makes the production and isolation of the polysaccharide very difficult.

A further disadvantage is that the polysaccharides released into the culture medium by microbial cells often co-purify with protein components of the culture medium or with proteins produced by the cultured cells. These protein contaminants require the use of additional purification steps prior to hydrolysis of the polysaccharide. Upon isolation of polysaccharides from plants or microbes, the processing of polysaccharides requires dissolution in solvents. This polysaccharide/solvent mixture is also a highly viscous material that is difficult to manipulate. Further, hydrolysis of polysaccharides may be incomplete, or the hydrolysis steps may result in partial destruction of the rhamnose product. Thus, yields of rhamnose from polysaccharides may be so low as to be unsuitable for large-scale production.

The preparation of rhamnolipids, effective as surfactants and emulsifiers, has been previously described. C. Syldatk et al., *Z. Naturforsch.* 40c:51-60, 1985; C. Syldatk et al., *Z. Naturforsch.* 40c:61-67, 1985. Efficient production of rhamnolipids from microbial sources generally employs a culture medium containing excess levels of carbon and phosphorus, but limiting concentrations of nitrogen and/or trace metals. A water-soluble carbohydrate, such as glucose, is usually used as a carbon source. In addition, optimal production of rhamnolipids is obtained from resting, rather than growing, cells. Typical yields of rhamnolipids according to these conditions range from 0.5-2.0 gm/l using continuous culture conditions. L. Kappeli et al., Ep Pat. Appl. 84109278.6, Aug. 4, 1984; L. GuerraSantos et al., *Appl. Environ. Microbiol.* 48:301-305, 1984.

Several rhamnose-containing compounds have been described, and have been recognized as possessing beneficial properties. These compounds have proven useful or are potentially useful as emulsifiers, biosurfactants, gelling agents, or stabilizers. Although attempts have been made to use rhamnose-containing polysaccharides as a source of rhamnose, these efforts have met with many difficulties. Therefore, there is a need in the art for a method for large-scale production of rhamnose from a microbial source. The present invention fulfills this need and further provides other related advantages.

DISCLOSURE OF THE INVENTION

Methods for large-scale production of rhamnose are disclosed. A preferred method comprises growing Pseudomonas sp. capable of production of high levels of rhamnolipid in a defined culture medium containing corn oil and isolating said rhamnolipid from said culture medium. The rhamnolipid is then hydrolyzed to produce rhamnose and a fatty acid and the rhamnose is separated therefrom. Preferred Pseudomonas sp. is *Pseudomonas aeruginosa* with strains selected from the group consisting of UI 29791, UI 220-7, UI 47074, and mutants thereof. The method also includes non-limiting concentrations of nitrogen compounds and magnesium compounds and limiting concentrations of iron compounds in the growth medium.

An alternative preferred embodiment is for a method of large scale production of rhamnose comprising growing *Pseudomonas aeruginosa* capable of production of high levels of rhamnolipid in a defined culture medium containing vegetable oil and isolating said rhamnolipid from said culture medium. The rhamnolipid is then hydrolyzed to produce rhamnose and 3-hydroxydecanoic acid, and the rhamnose is separated from the acid and purified.

BRIEF DESCRIPTION OF THE DRAWINGS

FIG. 1 shows the structure of rhamnolipids R1-R4, known to be synthesized by Pseudomonas sp. according to literature data.

FIG. 2 illustrates growth of *Pseudomonas aeruginosa* strain UI 29791 by batch fermentation, and resultant rhamnolipid production. ●, dry cell weight (g/l); ⊙, rhamnose (g/l).

FIG. 3 depicts growth of *Pseudomonas aeruginosa* strain UI 29791 by semicontinuous fermentation, and resultant rhamnolipid production. ●, dry cell weight (g/l); ⊙, rhamnose (g/l).

BEST MODE FOR CARRYING OUT THE INVENTION

The prior art teaches that rhamnose is primarily prepared by extraction of plant material, such as oak bark or citrus peels. A potential alternative source of rhamnose is rhamnose-containing polysaccharides, but preparation of rhamnose from this source is accompanied by obstacles that make the feasibility of this method questionable.

Although rhamnolipids have been described in the literature as biosurfactants and emulsifiers, rhamnolipids have not been previously suggested as a potential source of rhamnose. Production of rhamnolipids from Pseudomonas sp. generally utilizes a culture medium that contains a water-soluble carbohydrate, in particular glucose, as a carbon source, and limiting concentrations of nitrogen. GuerraSantos et al., supra; Kappeli et al., supra. Typical yields of rhamnolipid isolated under these conditions range from 0.5-2.0 g/l (corresponding to approximately 0.25-1.0 g/l rhamnose) when continuous culture techniques are employed. Guerra-Santos et al., supra; Kappeli et al., supra. Others have reported rhamnolipid yields of 13 g/l from Pseudomonas sp. grown with n-alkanes, soybean or olive oil, glycerol, or glucose as carbon sources. F. Wagner et al., EP Pat. Appl. 153,634, Sept. 4, 1985; C. Syldatk et al., *Z. Naturforsch.* 40c:61-67, 1985.

The present invention describes the production of rhamnose from rhamnolipids of *Pseudomonas aeruginosa*. The strains utilized for the production of rhamnose according to the present invention have been selected for increased production of rhamnolipids. The structures of rhamnolipids R1-R4, known to be synthesized by *Pseudomonas aeruginosa*, are depicted in FIG. 1. The selected high rhamnose-producing strains are cultivated in defined culture medium. The use of defined medium avoids the presence of uncharacterized proteins and nutrients in the environment from which rhamnolipids are isolated. In addition, defined medium produces less variability in microbial growth characteristics, which may occur with different lots or sources of complex medium.

The defined medium incorporates a vegetable oil as a carbon source, with corn oil a preferred vegetable oil. One advantage provided by corn oil is its ready availability and low cost. Further, the omission of water-soluble glucose as a carbon source avoids potential sugar contamination of the final rhamnose product. In contrast, corn oil is water-insoluble, and can be easily separated from the spent growth medium prior to isolation of rhamnolipid. Within the present invention, vegetable oils are added to the defined medium at a concentration of 20-100 g/l, with a concentration of 75 g/l preferred.

A source of phosphorous is also added to the defined medium, with potassium phosphate, potassium hydrogen phosphate, potassium dihydrogen phosphate, and mixtures thereof preferred as a phosphorous source. A preferred phosphorous concentration is 0.25-2.0 g/l, with 1.6 g/l particularly preferred. The medium also contains magnesium, preferably magnesium sulfate, at a magnesium concentration of 0.004-0.21 g/l, with 0.01 g/l magnesium preferred. A mixture of trace metals is also added to the medium at 1 to 3 times the concentration described in Table 2, infra.

Rhamnolipid production may be modified by growth of Pseudomonas sp. in culture medium containing limiting concentrations of iron. Additional iron may then be added during the fermentation at 1-3 times the initial concentration. When iron is added during the latter stages of the fermentation, oxygen uptake increases sharply, as indicated by an oxygen monitor on the fermentation apparatus.

A nitrogen source, preferably sodium nitrate or ammonium chloride, is also incorporated in the defined medium. In contrast to the published literature, however, the defined medium of the present invention does not utilize limiting concentrations of nitrogen. Within the present invention, nitrogen concentrations ranging from 0.6-3.2 g/l are preferred, with 2.5 g/l being particularly preferred.

In instances where the Pseudomonas strains are grown in a fermentor, the various defined medium components discussed above may either be added to the culture medium in batches or continuously, in order to achieve high rhamnose levels.

The pH of the medium is preferably maintained within a range of 5.0-7.5, with a pH of 6.5 particularly preferred. During the course of fermentation, the pH of the culture medium is maintained at the desired level by constant monitoring and adjustment through the addition of either sterile sodium hydroxide or sulfuric acid. Sterile air is sparged into the fermentor at a rate of 0.1 to 1.0 VVM (volume air per volume fermentor liquid per minute), with a rate of 0.5 VVM preferred. The level of dissolved oxygen within the defined medium may vary between 1% and 100% of saturation. The defined medium may also incorporate an antifoaming agent. For instance, Antifoam B (Sigma Chemical Co., St. Louis, MO) may be added at a concentration of 4-32 ml/l, preferably at a concentration of 10 ml/l.

Rhamnolipid is produced by both logarithmic phase and stationary phase Pseudomonas cultures, when grown according to the methods described herein. This is in contrast to previous reports on the production of rhamnolipid by Pseudomonas sp., which achieved overproduction of rhamnolipid only in stationary phase under conditions of nitrogen limitation.

The temperature of the medium is preferably maintained at approximately 37° C., but the temperature may range from 30° C. to 43° C.

Rhamnolipid is recovered from the spent culture medium by first separating the microbial cells from the medium, preferably through centrifugation. The supernatant is adjusted to a pH in the range of 2.0–4.0, with a preferred pH of 3.0. The pH is adjusted with a suitable acid, preferably sulfuric acid. The supernatant is then chilled to 0° C–20° C., with a preferred temperature of 4° C., in order to precipitate the rhamnolipid. The rhamnolipid can then be recovered by a variety of current methods, such as filtration or centrifugation. Alternatively, extraction may be performed either before or after precipitation of rhamnolipid. Rhamnolipid precipitation can also be accomplished by addition of calcium or zinc ions in the form of their salts, e.g., $CaCl_2$, in a concentration sufficient to precipitate the rhamnolipid. Precipitated rhamnolipid may then be isolated by filtration or centrifugation. Extraction of rhamnolipid may utilize a water-immiscible organic solvent, such as ethyl acetate or butyl acetate.

The isolated rhamnolipid is then hydrolyzed by heating the preparation in the presence of acid, producing rhamnose and hydroxydecanoic acid. The preferred temperature range for heating is 30° C.–100° C., and a preferred acid is sulfuric acid. The 3-hydroxydecanoic acid may be removed by extraction into an organic solvent or by ion exchange chromatography. A preferred organic solvent for extraction is ethyl acetate. For ion exchange chromatography, the rhamnose/hydroxydecanoic mixture is adjusted to a pH greater than 5.0, with a pH of 7.0 preferred. The mixture is then passed through an anion exchange resin.

The rhamnose product may be either crystallized from an aqueous solution or isolated from a solvent/water solution. The latter isolation may be accomplished by adjusting the pH of the solution to 7.0, if necessary, prior to evaporation of the solution. In addition, the 3-hydroxydecanoic acid component of the rhamnolipid hydrolysis may be recovered by elution from the anion exchange resin or by evaporation of the solvent in which it was extracted.

The levels of rhamnolipid produced by the methods of the present invention are significantly higher than those previously reported in the literature. As a result, much higher yields of the rhamnose end product are attainable. For instance, 15–24 g/l of rhamnose have been produced according to the methodology described, which corresponds to levels of rhamnolipid approximating 30–50 g/l. This yield of rhamnolipid is about 330% greater than the highest yield of rhamnolipid previously reported.

To summarize the examples which follow, Example I describes the isolation of *Pseudomonas aeruginosa* strains selected for overproduction of rhamnolipids. Example II presents the conditions utilized for growth of these rhamnolipid-overproducing strains. The production of rhamnose through batch fermentation of Pseudomonas strains is described in Example III. The production of rhamnose by the technique of semicontinuous fermentation is illustrated by Example IV. Example V described the production of 3-hydroxydecanoic acid from rhamnolipid.

The following examples are offered by way of illustration, and not by way of limitation.

EXAMPLE I

Isolation of *Pseudomonas aeruginosa* Strains

Pseudomonas strains utilized within the present invention were originally obtained either from human patients or from water samples. Briefly, clinical or water samples were inoculated into liquid medium conducive to the growth of blood cultures and incubated for 18–72 hours at 37° C. Aliquots of each culture were then plated onto chocolate agar plates and incubated for 18–48 hours at 37° C. Colonies growing on chocolate agar plates were identified as Pseudomonas on the basis of several criteria. First, Pseudomonas strains yield positive oxidase test results. Briefly, the oxidase test involves mixing a small amount of a bacterial colony grown on nutrient agar with fresh oxidase reagent (1% tetramethyl-p-phenylenediamine) on filter paper; a dark purple color is a positive reaction. Second, Gram stained Pseudomonas isolates morphologically appear as Gram negative rods. Third, a battery of nutritional/biochemical tests is used to positively identify Pseudomonas isolates. For instance, a battery of such tests has been incorporated into the Vitek analysis system (McDonnell-Douglas Corp.).

Upon positive identification of isolates as Pseudomonas, the strains were routinely stored on nutrient agar slants and transferred approximately once a month. Pseudomonas strains that were found to produce high levels of rhamnose via shake flask cultures using glucose or corn oil as a carbon source were further characterized by means of the API analysis system (Analytab Products, Plainview, NY). The API system permits simultaneous performance of 23 standard biochemical tests from an isolated colony on bacterial plating medium, leading to identification of Enterobacteriaceae, as well as other Gram negative bacteria, within 18–48 hours.

TABLE 1

Characterization of UI Strains 29791, 220-7 and 47074 as *Pseudomonas aeruginosa* Species[a]

| Test | Result 29791, 220-7 | 47074 |
|---|---|---|
| β-galactosidase | − | − |
| Arginine dihydrolase | + | + |
| Lysine decarboxylase | − | − |
| Ornithine decarboxylase | − | − |
| Citrate as a carbon source | + | + |
| $H_2S$ production | − | − |
| Urease | − | − |
| Tryptophan deaminase | − | − |
| Indole formation | − | − |
| Gelatinase | + | + |
| Glucose → acid | − | + |
| Mannitol → acid | − | − |
| Inositol → acid | − | − |
| Sorbitol → acid | a | − |
| Rhamnose → acid | − | − |
| Sucrose → acid | − | − |
| Melibiose → acid | − | + |
| Amygdalin → acid | + | − |
| Arabinose → acid | + | + |

[a]All strains grew at 42° C. on nutrient agar plates, which is not part of the API test. The results for 29791 and 220-7, when compared to data supplied with the API system, give excellent identification (the expected frequency of occurrence is once in 68 strains tested) for a Pseudomonas of the "fluorescent group," which includes *Ps. aeruginosa*, *Ps. fluorescens* and *Ps. putida*; strain 47074 also gave anexcellent identification for a Ps. of the fluorescent group (frequency of occurrence of one in 1765 strains). The Manual of Clinical Microbiology (E. H. Lennette, ed., 1980) states that only *Ps. aeruginosa* will grow at 42° C., while the other two species will not. Additionally, the applicants have demonstrated some acid production from glucose with both flask and fermentor cultures (data not shown). Thus, if the API test on 29791 and 220-7 had produced apositive result for glucose → acid, it would have identified these strains as *Ps. aeruginosa* (expected frequency of occurrence of one in 49 strains tested). Therefore, our strains do not belong in another one of the fluorescent group of Pseudomonas, but do appear to be unusual strains of *Ps. aeruginosa*.

EXAMPLE II

Growth of Rhamnolipid-Producing Strains

*Pseudomonas aeruginosa* strain 29791 was grown in 500 ml shake flasks, each flask containing 50 ml of defined medium as described in Table 2, infra, and as modified in the footnote to Table 3.

TABLE 2

M-5 Medium Composition

| Medium Component | Concentration (g/l) |
|---|---|
| $NaNO_3$ | 15 |
| KCl | 1.1 |
| NaCl | 1.1 |
| $FeSO_4.7H_2O$ | 0.00028 |
| Trace elements* | (5 ml) |
| $Ca(NO_3)_2.4H_2O$ | 0.01 |
| $KH_2PO_4$ | 3.4 |
| $K_2HPO_4$ | 4.4 |
| $MgSO_4.7H_2O$ | 0.5 |
| (pH adjusted to | 6.5) |
| Corn oil | 75.0 |

*Trace elements

| Component | g/l |
|---|---|
| $ZnSO_4.7H_2O$ | 0.29 |
| $CaCl_2.4H_2O$ | 0.24 |
| $CoCl_2.6H_2O$ | 0.24 |
| $CuSO_4.5H_2O$ | 0.25 |
| $MnSO_4.H_2O$ | 0.17 |

The cultures were grown at 37° C. with a gyratory rate of 200 rpm. After 6 days of culture, the cells obtained the desired cell density. Samples were removed and the dry weight of cells was determined by first centrifuging the samples. The cell pellets were resuspended in water, placed in a preweighed container, and dried in an oven to a constant weight. The cell free culture medium was then centrifuged at 6000×g for 30 min at 4° C., and the supernatant was collected. Rhamnolipid concentration was determined by measuring rhamnose in the culture supernatant. The results are shown in Table 3.

TABLE 3

Growth of *Pseudomonas aeruginosa* strain 29791 in Medium M-2[b] Containing Glucose, Corn Oil, or Both

| Carbon Source | Rhamnose (g/l) | Dry Cell Weight (g/l) |
|---|---|---|
| 75 g/l glucose | 0.5 | 2.3 |
| 40 g/l corn oil | 5.4 | 5.2 |
| 37 g/l glucose + 20 g/l corn oil | 0.2 | 2.3 |

[b]Medium M-2 is identical to M-5, except for the following modification: $NaNO_3$ (12.2 g/l); $KH_2PO_4$ (6.8 g/l); $K_2HPO_4$ (8.7 g/l); pH 7.5. The only carbon source present in the growth medium is that indicated in the Table. The values were obtained with growth of a 140 ml volume of cells.

As depicted in Table 3, growth of *Pseudomonas aeruginosa* strain 29791 in the presence of corn oil alone produced significantly increased levels of both cellular mass and rhamnose. The increase in rhamnose cannot be attributed solely to the presence of more cells, since cell mass was 2.25 times greater when corn oil alone was used as the carbon source, while rhamnose levels were approximately 10–30 times greater when corn oil alone was used.

EXAMPLE III

Production of Rhamnose by Batch Fermentation

Strain 29791 was grown in a 14 l fermentor containing 6 l of defined medium. The medium had a composition as shown in Table 2 but was modified by the addition of components, as indicated below. The culture was incubated at 37° C., and the pH was maintained between 5.5 and 7.0 by the addition of either sodium hydroxide or sulfuric acid. An aeration rate of 0.5 VVM, a dissolved oxygen level of 25%–90% saturation, and an agitation rate of 450–550 rpm were maintained. Samples were periodically taken over 10 days of culture, and the results of the fermentation are shown in FIG. 2. At 27 and 76 h, magnesium, iron, calcium, and trace elements were added at concentrations equal to those originally present in M-5 medium. The maximum cell density of 15 g/l was achieved at day 5, and the maximal rhamnose level of 23 g/l, corresponding to approximately 46 g/l rhamnolipid, was obtained at day 8. The volumetric productivity over the first 8 days of culture was 5.8 g rhamnolipid/1-day.

Culture suspension from a 6 l fermentor batch was centrifuged (45 min at 6000 xg) to remove cells, and the supernatant was adjusted to pH 2.5 with sulfuric acid prior to storage overnight at 4° C. This solution (2.6 g rhamnose total) with its resulting precipitate was centrifuged as above in order to separate a precipitate of rhamnolipid (1.9 g rhamnose total). The rhamnolipid precipitate was resuspended in 300 ml of 1M $H_2SO_4$ and heated for 2 hours at 100° C. This hydrolysis mixture was treated once with 4 volumes of ethyl acetate, yielding 1.2 g rhamnose in the aqueous layer (representing free rhamnose) and 0.5 g rhamnose in the organic layer (containing remaining rhamnolipid and 3-hydroxydecanoic acid). The rhamnose can be further purified by neutralization with NaOH, reextraction with ethyl acetate, and crystallization.

Alternatively, the original cell-free supernatant acidified to pH 3, or the precipitated pellet suspended in water at pH 3, can be successfully extracted with 4 volumes of ethyl acetate with an 80–90% yield.

EXAMPLE IV

Production of Rhamnose by Semicontinuous Fermentation

Using the same medium and volumes described in Example III, strain 29791 was grown by semicontinuous fermentation. However, the addition of magnesium, iron, calcium, and trace elements occurred at 15 h, and one-fourth the original nitrogen level was added at 19 h. Over a 4-day incubation period, 1.5 liters (one-fourth the working volume) of culture medium were removed and replaced with fresh medium at 47 h and 75 h. Rhamnolipid can be recovered from the culture supernatant as described in Example III. The data resulting from semicontinuous fermentation are shown in FIG. 3. Taking into account the rhamnolipid removed with the culture medium that was replaced at 47 h and 75 h, the overall productivity was 6.4 g rhamnolipid/1-day. From the time of the first medium removal and until approximately maximal cell mass was obtained, production rates of about 10 g rhamnolipid/1-day were maintained. Rhamnose was recovered by hydrolysis, according to the procedure described in Example III above.

EXAMPLE V

Production of 3-Hydroxydecanoic Acid by Hydrolysis of Rhamnolipid

Rhamnolipid recovered from the culture supernatant, as described in Examples III and IV, may be processed so as to facilitate the recovery of 3-hydroxydecanoic acid. Briefly, 100 mg of rhamnolipid R3, as depicted in FIG. 1, was mixed with 1.0 ml of a 1:1 mixture of 1N $H_2SO_4$ and dioxane. The suspension was stirred at 110° C., the temperature being maintained in an oil bath, and the reaction was monitored by HPTLC. As the hydrolysis reaction progressed, a second liquid phase formed. After approximately 4 hours of hydrolysis, the reaction mixture was cooled and the dioxane was evaporated. The aqueous phase was then extracted with diethylether. The extract was dried with $Na_2SO_4$ and concentrated, yielding 50 mg (yellow oil) of 3-hydroxydecanoic acid [GC-MS:m/z 89 (base peak), 71, 69, 55, 43; FAB-MS:m/z 189 (M+H), 171, 153] and 3 [(3-hydroxydecanoyloxy)]decanoic acid [FAB-MS:m/z 381 (M+Na), 359 (M+H)].

A similar procedure can be used for production of 3-hydroxydecanoic acid from rhamnolipid R1 as depicted in FIG. 1. The hydrolysis reaction is performed as described for rhamnolipid R3, but hexane is used for extraction of the aqueous phase (rather than diethylether).

From the foregoing, it will be appreciated that, although specific embodiments of the invention have been described herein for purposes of illustration, various modifications may be made without deviating from the spirit and scope of the invention. Accordingly, the invention is not to be limited except as by the appended claims.

We claim

1. A process for large-scale production of rhamnose and 3-hydroxydecanoic acid, comprising:
   growing Pseudomonas sp. capable of production of high levels of rhamnolipid in a defined culture medium containing corn oil as a carbon source;
   isolating said rhamnolipid from said culture medium at a concentration from about 30 g/l to about 50 g/l;
   hydrolyzing said rhamnolipid so as to produce rhamnose and 3-hydroxydecanoic acid; and
   separating said rhamnose and said hyhdroxydecanoic acid.

2. The process of claim 1, further comprising, after the step of separating, purifying said rhamnose.

3. The process of claim 1 wherein Pseudomonas sp. is *Pseudomonas aeruginosa*.

4. The process of claim 3 wherein said *Pseudomonas aeruginosa* is a strain selected from the group consisting of UI 29791, UI 220-7, and UI 47074.

5. The process of claim 3 wherein said *Pseudomonas aeruginosa* is a strain selected from the group consisting of mutants of UI 29791, UI 220-7, and UI 47074.

6. The process of claim 1 wherein said defined culture medium contains a non-limiting concentration of a nitrogen compound.

7. The process of claim 6 wherein said non-limiting concentration of a nitrogen compound ranges from approximately 0.6 to approximately 3.2 grams of nitrogen per liter.

8. The process of claim 7 wherein said non-limiting concentration of a nitrogen compound is approximately 2.5 grams of nitrogen per liter.

9. The process of claim 6 wherein said nitrogen compound is selected from the group consisting of sodium nitrate and ammonium chloride.

10. The process of claim 1 wherein said defined culture medium contains a limiting concentration of an iron compound.

11. The process of claim 1 wherein said defined culture medium contains magnesium ion concentrations ranging from approximately 0.004 g/l to approximately 0.21 g/l.

12. The process of claim 1 wherein said defined culture medium contains a phosphate compound selected from the group consisting of potassium phosphate, potassium hydrogen phosphate, and potassium dihydrogen phosphate.

13. The process of claim 12 wherein said phosphate compound is present at a phosphorous concentration ranging from approximately 0.25 to approximately 2.0 g/l.

14. The process of claim 13 wherein said phosphate compound is present at a phosphorous concentration of approximately 1.6 g/l.

15. The process of claim 1 wherein said defined culture medium includes the components and concentrations set forth in Table 2.

16. A process for large-scale production of rhamnose and 3-hydroxydecanoic acid, comprising:
    growing *Pseudomonas aeruginosa* capable of productions of high levels of rhamnolipid in a defined culture medium containing vegetable oil as a carbon source;
    isolating said rhamnolipid from culture medium at a concentration from about 30 g/l to about 50 g/l;
    hydrolyzing said rhamnolipid so as to produce rhamnose and 3-hydroxydecanoic acid; and
    separating said rhamnose and said 3-hydroxydecanoic acid.

17. The process of claim 16, further comprising, after the step of separating, purifying said rhamnose.

18. The process of claim 16 wherein said *Pseudomonas aeruginosa* is a strain selected from the group consisting of UI 29791, UI 220-7, and UI 47074.

19. The process of claim 16 wherein said *Pseudomonas aeruginosa* is a strain selected from the group consisting of mutants of UI 29791, UI 220-7, and UI 47074.

20. The process of claim 16 wherein said vegetable oil is corn oil.

21. The process of claim 16 wherein said vegetable oil is present at a concentration ranging from approximately 20 to approximately 100 g/l.

22. The process of claim 16 wherein said vegetable oil is present at a concentration of approximately 75 g/l.

23. The process of claim 16 wherein said defined culture medium contains a non-limiting concentration of a nitrogen compound.

24. The process of claim 23 wherein said non-limiting concentration of a nitrogen compound ranges from approximately 0.6 to approximately 3.2 grams of nitrogen per liter.

25. The process of claim 24 wherein said non-limiting concentration of a nitrogen compound is approximately 2.5 grams of nitrogen per liter.

26. The process of claim 23 wherein said nitrogen compound is selected from the group consisting of sodium nitrate and ammonium chloride.

27. The process of claim 16 wherein said defined culture medium contains a limiting concentration of an iron compound.

28. The process of claim 16 wherein said defined culture medium contains a non-limiting concentration of a magnesium compound.

29. The process of claim 16 wherein said defined culture medium contains a phosphate compound selected from the group consisting of potassium phosphate, potassium hydrogen phosphate, and potassium dihydrogen phosphate.

30. The process of claim 29 wherein said phosphate compound is present at a phosphorous concentration from approximately 0.25 to approximately 2.0 g/l.

31. The process of claim 30 wherein said phosphate compound is present at a phosphorous concentration of approximately 1.6 g/l.

32. The process of claim 16 wherein said defined culture medium includes the components shown in Table 2.

33. A process for large-scale production of rhamnose and 3-hydroxydecanoic acid, comprising:

growing *Pseudomonas aeruqinosa* strain UI 29791, capable of production of high levels of rhamnolipid throughout the growth cycle, in a defined culture medium including approximately 75 g/l corn oil, 2.5 g/l nitrogen, 1.6 g/l phosphorous, 10 ml/l antifoaming agent, and limiting concentrations of iron and non-limiting concentrations of magnesium at a pH of approximately 6.5, with sterile air sparged into the medium at 0.5 VVM;

isolating said rhamnolipid from said culture medium;

hydrolyzing said rhamnolipid by heating at 30° C.–100° C. in the presence of sulfuric acid so as to produce rhamnose and 3-hydroxydecanoic acid;

separating said rhamnose and said 3-hydroxydecanoic acid; and purifying said rhamnose.

* * * * *